United States Patent
Kelly

(10) Patent No.: US 6,642,212 B1
(45) Date of Patent: *Nov. 4, 2003

(54) HEALTH SUPPLEMENTS CONTAINING PHYTO-OESTROGENS, ANALOGUES OR METABOLITES THEREOF

(75) Inventor: Graham Edmund Kelly, Northbridge (AU)

(73) Assignee: Novogen Research Pty. Ltd. (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/421,069

(22) Filed: Oct. 19, 1999

Related U.S. Application Data

(63) Continuation of application No. 08/910,837, filed on Aug. 13, 1997, now Pat. No. 6,562,380, which is a continuation of application No. 08/338,567, filed as application No. PCT/AU93/00230 on May 19, 1993, now Pat. No. 5,830,887.

(30) Foreign Application Priority Data

May 19, 1992 (AU) .............................. PL 2511

(51) Int. Cl.⁷ .................. A01N 43/04; A11K 31/70; C07D 311/04; C07D 311/74
(52) U.S. Cl. .................. 514/54; 514/25; 514/182; 424/195.1; 424/423; 424/449; 424/451; 424/464; 426/545; 549/403; 549/406; 525/404
(58) Field of Search .............. 514/54, 182, 25; 252/404; 424/195.1, 464, 423, 449, 451; 426/545; 549/403, 406; 525/404

(56) References Cited

U.S. PATENT DOCUMENTS

| | | | |
|---|---|---|---|
| 3,973,608 A | 8/1976 | Umezawa et al. | 195/80 |
| 4,200,692 A | 4/1980 | Puls et al. | |
| 4,264,509 A | 4/1981 | Zilliken | |
| 4,301,251 A | 11/1981 | Rumyantseua et al. | 435/267 |
| 4,366,082 A | 12/1982 | Zilliken | |
| 4,390,559 A | 6/1983 | Zilliken | 426/545 |
| 5,141,746 A | 8/1992 | Fleury et al. | 424/195.1 |
| 5,320,949 A | 6/1994 | Shen | 435/68.1 |
| 5,352,384 A | 10/1994 | Shen | 252/398 |
| 5,498,631 A * | 3/1996 | Gorbach et al. | |
| 5,506,211 A | 4/1996 | Barnes et al. | 514/27 |
| 5,516,528 A | 5/1996 | Hughes et al. | |
| 5,530,112 A | 6/1996 | Greenshields et al. | 536/123.1 |
| 5,547,866 A | 8/1996 | Durzan et al. | 435/123 |
| 5,554,519 A | 9/1996 | Weber et al. | 435/125 |
| 5,637,561 A | 6/1997 | Shen et al. | 514/2 |
| 5,679,806 A | 10/1997 | Zheng et al. | 549/403 |
| 5,700,669 A | 12/1997 | Hanson et al. | 435/123 |
| 5,726,034 A | 3/1998 | Bryan et al. | 435/68.1 |
| 5,763,389 A | 6/1998 | Shen et al. | 514/2 |
| 5,789,581 A | 8/1998 | Matsuura et al. | 536/128 |
| 5,792,503 A | 8/1998 | Gugger et al. | 426/634 |
| 5,830,887 A * | 11/1998 | Kelly | |
| 6,340,703 B1 | 1/2002 | Kelly | |
| 6,497,906 B1 | 12/2002 | Kelly | |
| 6,562,380 B1 | 5/2003 | Kelly | |

FOREIGN PATENT DOCUMENTS

| | | |
|---|---|---|
| AU | A-24813/97 | 6/1997 |
| EP | 0129667 | 1/1985 |
| EP | 0135172 | 3/1985 |
| EP | 0136569 | 4/1985 |
| EP | 0426998 A2 | 5/1991 |
| GB | 1482238 | 8/1977 |
| JP | 61246124 A | 11/1986 |
| JP | 62-106016 | 5/1987 |
| JP | 62126186 A | 6/1987 |
| JP | 1258669 | 10/1989 |
| JP | 01258669 A | 10/1989 |
| JP | 267218 | 3/1990 |
| JP | 02069165 A | 3/1990 |
| JP | 2160722 | 6/1990 |
| JP | 03047049 A | 2/1991 |
| WO | WO93/23069 | 11/1993 |
| WO | WO94/23716 | 10/1994 |

OTHER PUBLICATIONS

Naim, Michael, Treatise, The Isolation, Characterization and Biological Activity of Isoflavones from Soybeans, Submitted to the Senate of the Hebrew University of Jerusalem—Oct. 1974.
EPO Examination Report dated Mar. 8, 2002.
Sharma, R.D., "Effect of various isoflavones on lipid levels in triton–treated rats", Atherosclerosis 33, 1979, p. 271–375.
PAJ Abstract corresponding to JP1042427 A (Feb. 14, 1989).
U.S. patent application Ser. No. 09/421,069, Kelly, filed Oct. 19, 1999.
U.S. patent application Ser. No. 09/602,191, Kelly, filed Jun. 22, 2000.
U.S. patent application Ser. No. 09/986,509, Kelly, filed Nov. 9, 2001.
U.S. patent application Ser. No. 10/274,371, Kelly, filed Oct. 21, 2002.
Grunert et al. Deutsche Tierarztliche Wochenschrift, 74. Jahrgang 1967, p. 431–433.*
Weinberg et al. Journal of High Resolution Chromatography, 1992, XP–001056155.*
The Merck Index, 8ᵗʰ Ed., "Geinstein", "Daidzein", and "Formononetin," pp. 320, 484 and 469–470 [respectively], (1968).

(List continued on next page.)

*Primary Examiner*—James O. Wilson
*Assistant Examiner*—Patrick Lewis
(74) *Attorney, Agent, or Firm*—Finnegan, Henderson, Farabow, Garrett & Dunner, L.L.P.

(57) ABSTRACT

Compositions enriched with natural phyto-oestrogens or analogues thereof selected from Genistein, Diadzein, Formononectin and Biochanin A. These compositions may be used as food additives, tablets or capsules for promoting health in cases of cancer, pre-menstrual syndrome, menopause or hypercholesterolaemia.

22 Claims, No Drawings

OTHER PUBLICATIONS

Walz, E., "Isoflavon–und Saponin–Glucoside in Soja Hispida," *Justus Liebigs Am. Chem.*, vol. 489, pp. 118–155 (1931).

Y. Liu et al., Chemical Abstracts, 115 (8): Abstract No. 78763p, p. 466 (1991).

Adlercreutz, H. et al., "Determination of Urinary Lignans and Phytoestrogen Metabolites, Potential Antiestrogens and Anticarcinogens, in Urine of Women on Various Habitual Diets," *J. Steroid Biochem*, vol. 25, No. 58, pp. 791–797 (1986).

Aldercreutz, Herman et al., "Dietary Phytoestrogens and Cancer In Vitro and In Vivo Studies," *J. Steroid Biochem Molec. Biol.*, vol. 41, No. 3–8 pp. 331–337 (1972).

Adlercreutz, Herman et al., "Dietary phyto–oestrogens and the menopause in Japan," *The Lancet*, pp. 1233 (1992).

Adlercreutz, H. et al., "Excretion of the Lignans Exterolactone and Enterodiol and of Equol in Omnivorous and Vegetarian Postmenopausal Women and in Women with Breast Cancer," *The Lancet*, pp. 1295–1299 (1982).

Adlercreutz, H., "Lignans and Phytoesrogens", *Front. gastrointest. Res.*, vol. 14, pp. 165–176 (1988).

Adlercreutz, Herman et al., "Urinary Excretion of Lignans and Isoflavonoids Phytoestrogens in Japanese Men and Women Consuming a Traditional Japanese Diet," *Am. J. Clin. Nutr.*, vol. 54, pp. 1093–1100 (1991).

Adlercreutz, Herman, "Western Diet and Western Diseases: Some Hormonal and Biochemical Mechanisms and Associations," *Scand. J. Clin. Lab. Invest*, Suppl., vol. 201 pp. 3–23 (1990).

Anderson M.D., James et al., "Meta–Analysis of the Effects of Soy Protein Intake on Serum Lipids," *New Eng. J. Med.*, vol. 333, No. 5, pp. 276–282 (1995).

Barnes, Stephen et al., "Soybeans Inhibit Mammary Tumors in Models of Breast Cancer," *Mutagens and Carcinogens in the Diet*, pp. 239–253 (1990).

Bailey, E.T. et al., "Isoflavone Concentrations in the Leaves of the Species of the Genus Trifolium, Section Calycomorphum," Aust. J. Agric. Res., vol. 22, No. 5, pp. 731–736 (1971).

Bannwart, Christoph et al., "Identification of the Isoflavonic Phytoestrogen daidzein in Human Urine," *Clinica Chimica Acta*, vol. 136, pp. 165–172 (1984).

Barrow, N.J., "Nutrient Potential and Capacity," *Aust. J. Agric. Res.*, vol. 17, pp. 849–861 (1966).

Barrow, N.J. et al., "Nutrient Potential and Capacity", *Aust. J. Agric. Res.*, 18:55–62 (1966).

Beck, A.B., "The Oestrogenic Isoflavones of Subterranean Clover," *Aust. J. Agric. Res.*, 15:223–230 (1964).

Beckham, N., "Menopause," *The Family Guide to Natural Therapies*, Greenhouse Publications, pp. 41–42, 50 (1988).

Beckham, Nancy, "Herbal Help to Avoid Menopause Symptoms," *Australian Wellbeing*, No. 29, pp. 74–76 (1988).

Beckham, Nancy, "Phyto–Oestrogens and Compounds that Affect Oestrogen Metabolism—Part I," *Aust. J. Med. Herbalism*, vol. 7, No. 1, pp. 11–16 (1995).

Beckham, Nancy, "Phyto–Oestrogens and Compounds that Affect Oestrogen Metabolism—Part II," *Aust. J. Med. Herbalism*, vol. 7, No. 2, pp. 27–33 (1995).

Bennetts, H.W. et al., "A Specific Breeding Problem of Sheep on Subterranean Clover Pastures in Western Australia," *The Australian Veterinary Journal*, vol. 22, pp. 2–12 (1946).

Bombardelli, Ezio, "Technologies for the Processing of Medicinal Plants," in *The Medicinal Plant Industry*, Chapt. 7, pp. 85–98 (1991).

Bradbury, R.B. et al., "The Chemistry of Subterranean Clover. Part I. Isolation of Formononetin and Genistein," *J. Chem. Soc.*, pp. 3447–3449 (1951).

Bradbury, R.B. et al., "Estrogens and Related Substances in Plants," in *Vitamins and Hormones Advances in Research and Applications*, Harris, R.S. et al., eds., pp. 207–233 (1954).

Brandi, M.L., "Flavonoids: biochemical effects and therapeutic applications," *Bone and Mineral*, vol. 19 (Suppl.) S3–S14 (1992).

Braden, A.W.H. et al., "Comparison of Plasma Phyto–Oestrogen Levels in Sheep and Cattle After Feeding on Fresh Clover," *Aust. J. Agric. Res.*, vol. 22, pp. 663–670 (1971).

Braden, A.W.H. et al. "The Oestrogenic Activity and Metabolism of Certain Isoflavones in Sheep," *Aust. J. Agric. Res.*, vol. 18 pp. 335–348 (1967).

Circle, S. J. et al., "Processing Soy Flours, Protein Concentrates and Protein Isolates," *Soybeans: Chemistry and Technology*, vol. 1, pp. 294–338 (1972).

Coward, Lori et al., "Genistein, Daidzein, and Their β–Glycoside Conjugates: Antitumor Isoflavones in Soybean Foods from American and Asian Diets," *J. Agric. Food Chem.*, vol. 41, pp. 1961–1967 (1983).

Davies, Lloyd H. et al., "Further Studies on Oestrogenic Activity in Strains of Subterranean Clover (*Trifolium Subterraneum* L.) In South–Western Australia," *Aust. J. Agric. Res.* vol. 16, No. 6, pp. 937–950 (1965).

Davis, Harold et al., "Extraction," *Bentley's Text–Book of Pharmaceuticals*, 6th ed., XVIII, pp. 272–273 (1956).

Düker, Eva–Maria et al., "Effects of Extracts from *Cliniciguga Racemosa* on Gonadotropin Release in Menopausal Women and Ovariectomized Rats," *Planta Med.*, vol. 57, pp. 420–424 (1991).

Eldridge, Arthur C., "Determination of Isoflavones in Soybeans Flours, Protein Concentrates, and Isolates," *J. Agric. Food. Chem.*, vol. 30, pp. 353–355 (1982).

Eldridge, A.C., "High–performance liquid chromatography separation of soybean iso–flavones and their glucosides," *J. Chrom.*, vol. 234 pp. 494–496 (1982).

Eldridge, Arthur C. et al., "Soybean Isoflavones: Effect of Environment and Variety on Composition," *Agric. Food Chem.*, vol. 31 pp. 394–396 (1983).

Farmakalidis, Efi et al., "Isolation of 6"–O–Acetylgenistin and 6"–O–Acetyldaidzin from Toasted Defatted Soyflakes," *J. Agric. Food Chem.*, vol. 33, pp. 385–389 (1985).

Farmakalidis et al., "Semi–Preparative High–Performance Liquid Chromatographic Isolation Soybean Isoflavones," *J. Chrom.*, vol. 295, pp. 510–514 (1984).

Farnsworth, Norman R. et al., "Potential Value of Plants as Sources of New Antifertility Agents II," *J. Pharm. Sciences*, vol. 64, No. 5, pp. 717–754 (1975).

Francis., C.M. et al., "The Distribution of Oestrogenic Isoflavones in the Genus Trifolium," *Aust. J. Agric. Res.*, 18:47–54 (1967).

Francis, C.M. et al., "Varietal Variation in the Isoflavone Content of Subterranean Clover: Its Estimation by a Microtechnique," *Aust. J. Agric. Res.*, 16:557–564 (1965).

Gildersleeve, Rhonda R. et al., "Screening Rose Clover and Subterranean Clover Germplasm for Isoflavones," *Crop. Sci.*, vol. 31 pp. 1374–1376 (1991).

Gildersleeve, Rhonda R. et al., "Detection of Isoflavones in Seedling Subterranean Clover," *Crop Sci.*, vol. 31, pp. 889–892 (1991).

Gladstones, J.S., "Naturalized Subterranean Clover Strains in Western Australia: A Preliminary Agronomic Examination," *Aust. J. Agric. Res.*, vol. 18, pp. 713–731 (1967).

Herman, C. et al., "Soybean Phytoestrogen Intake and Cancer Risk," *American Institute of Nutrition*, pp. 7575–7705 (1995).

Holt, S., "Selected Bibliography of Scientific Studies on Genistein and Other Soya Isoflavones," Soya for Health: *The Definitive Medical Guide*, pp. 159–170 (1996).

Jenkins, David J.A. et al., "Leguminous seeds in the dietary management of hyperlipidemia," *Am. J. Clin. Nut.*, vol. 38, pp. 567–573 (1983).

Jones, Amanda E. et al., "Development and Application of a High–Performance Liquid Chromatographic Method for the Analysis of Phytoestrogens," *J. Sci. Food Agric.*, vol. 46, pp. 357–364 (1989).

Kaldas, Rami S. et al., "Reproductive and General Metabolic Effects of Phytoestrogens in Mammals," *Reproductive Toxicology Review*, vol. 3, No. 2, pp. 81–89 (1989).

Kitada, Yoshimi et al., "Determination of Isoflavones in soy bean by high–performance liquid chromatography with amperometric detection," *J. Chrom.*, vol. 366, pp. 403–406 (1986).

Kitts, D.D. et al., "Uterine Weight Changes and $^3$H–Uridine Uptake in Rats Treated with Phytoestrogens," *Can. J. Anim. Sci.*, vol. 60 pp. 531–534 (1980).

Knuckles, Benny E. et al., "Coumestrol Content of Fractions Obtained During Wet Processing of Alfalfa," *J. Agric. Food Chem.*, vol. 24, No. 6, pp. 1177–1180, (1976).

Kudou, Shigemitsu et al., "A New Isoflavone Glycoside in Soybean Seeds (*Glycine max* Merrill), Glycitein 7–O–β–D–(6"–O–Acetyl)–Glucopyranoside," *Agric. Biol. Chem.*, vol. 55, No. 3, pp. 859–860 (1991).

Kudou, Shigemitsu et al., "Malonyl Isoflavone Glycosides in Soybean Seeds (*Glycine max* Merrill)," *Agric. Biol. Chem.*, vol. 55, No. 9, pp, 2227–2233 (1991).

Lindner, H.R., "Study of the Fate of Phyto–Oestrogens in the Sheep by Determination of Isoflavones and Coumestrol in the Plasma and Adipose Tissue," *Aust. J. Agric. Res.*, vol. 18, pp. 305–333 (1967).

Lock, Margaret, "Contested meanings of the menopause," *The Lancet*, vol. 337, pp. 1270–1272 (1991).

Martin, P.M. et al., "Phytoestrogen Interaction with Estrogen Receptors in Human Breast Cancer Cells," *Endocrinology*, vol. 193, No. 5, pp. 1860–1867 (1978).

Messina, Mark et al., "The Role of Soy Products in Reducing Risk of Cancer," *J. of National Cancer Institute*, vol. 83, No. 8, pp. 541–546 (1991).

Morris, P., "Identification and Accumulation of Isoflavonoids and Isoflavone Glucosides in Soybean Leaves and Hypocotyls in Resistance Responses to Phytophthora Megasperma f.sp. Glycinea," *Physiological and Molecular Plant Pathology*, 39 pp. 229–244 (1991).

Murphy, P.A., "Phytoestrogen Content of Processed Soybean Products," *Food Technology*, pp. 60–64 (1982).

Murphy, P.A., "Separation of Genistin, Daidzin and Their Aglucones, and Coumesterol by Gradient High Performance Liquid Chromatograpy," *J. Chrom*, vol. 211, pp. 166–169 (1991).

Naim, M. et al., "A New Isoflavone from Soya Beans," *Phytochemistry*, vol. 12, pp. 169–170 (1973).

Naim, M. et al., "Soybean Isoflavones, Characterization, Determination, and Antifungal Activity," *J. Agr. Food Chem.*, vol. 22, No. 5, pp. 806–810 (1974).

Nash, A.M. et al., "Fractionation and Characterization of Alcohol Extractables Associated with Soybean Proteins. Nonprotein Components," *J. Agr. Food Chem.*, vol. 15, No. 1, pp. 102–108 (1967).

Ohta, Naokazu et al., "Isoflavonoid Constituents of Soybeans and Isolation of a New Acetyl Daidzin," *Agric. Biol. Chem.*, 43, vol. No. 7, pp. 1415–1419 (1979).

Okano, Koji et al., "Isolation of Four Kinds of Isoflavon from Soya Bean," *Bron: Bull. Agr. Chem. Soc. Japan.* 15, vol. 15, p. 110 (1939).

Okubo, Kazuyoshi et al., "Components Responsible for the Undesirable Taste of Soybean Seeds," *Biosci. Biotech. Biochem.*, vol. 56, No. I, pp. 99–103 (1992).

Pope, G.S., "The Importance of Pasture Plant Oestrogens in the Reproduction and Lactation of Grazing Animals," *Dairy Science Abstracts*, vol. 16, No. 5, pp. 333–356 (1954).

Price, K.R. et al., "Naturally Occurring Oestrogens in Foods—A Review," *Food Additives and Contaminants*, vol. 2, No. 2 pp. 73–106 (1985).

Reinli, Kathrin et al., "Phytoestrogen Content of Foods—A Compendium of Literature Values," *Nutrition and Cancer*, vol. 26, No. 2, pp, 123–148 (1996).

Rose, David P., "Dietary Fiber, Phytoestrogens, and Breast Cancer," *Nutrition*, vol. 8, No. 1 (1992).

Rossiter, R.C., "Physiological and Ecological Studies on the Oestrogenic Isoflavones in Subterranean Clover (T. Subterraneum L.)," *Aust. J. Agric. Res.*, Chapter III, 18:23–37 (1967).

Rossiter, R.C., "Physiological and Ecological Studies on the Oestrogenic Isoflavones in Subterranean Clover (T. Subterraneum L.)," *Aust. J. Agric. Res.*, Chapter IV, 18:39–46 (1966).

Seo, A. et al., "Improved High–Performance Liquid Chromatographic Analysis of Phenolic Acids and Isoflavonoids from Soybean Protein Products," *J. Agric. Food Chem.*, vol. 32, No. 3, pp. 530–533 (1984).

Setchell, K.D.R. et al., "High–Performance Liquid Chromatographic Analysis of Phytoestrogens in Soy Protein Preparations with Ultraviolet, Electrochemical and Thermospray Mass Spectrometric Detection," *J. Chrom.*, vol. 386 pp. 315–323 (1987).

Setchell, K.D.R. et al., "Mammalian Lignans and Phyto–oestrogens Recent Studies on their Formation, Metabolism and Biological Role in Health and Disease," in Role of the Gut Flora In Toxicity and Cancer, pp. 315–339 (1988).

Setchell, KDR et al., "Nonsteroidal estrogens of dietary origin: possible roles in hormone–dependent disease," *Am. J. Clin. Nut.*, vol. 40 pp. 569–578 (1984).

Shimoyamada, Makoto et al., "Saponin Composition in Developing Soybean Seed (*Glycine max* (L.) Merrill, cv. Mikuriyaao)," *Agric. Biol. Chem.*, vol. 55, No. 5, pp. 1403–1405 (1991).

Shutt, Donald A., "The Effects of Plant Oestrogens on Animal Reproduction," *Endeavour*, vol. 35, pp. 110–113 (1976).

Shutt, D.A. et al., "Free and Conjugated Isoflavones in the Plasma of Sheep Followed Ingestion of Oestrogenic Clover," *Aust. J. Agric. Res.*, vol. 18, pp. 647–655 (1967).

Shutt, D.A., "Interaction of Genistein With Oestradiol in the Reproductive Tract of the Ovariectomized Mouse," *J. Endrocrin.*, vol. 37, pp. 231–232 (1967).

Shutt, D.A. et al., "Quantitative Aspects of Phyto–Oestrogen Metabolism in Sheep Fed on Subterranean Clover (*Trifolium Subterraneum* Cultivar Clare) or Red Clover (*Trifolium Pratense*)," *Aust. J. Agric. Res.*, vol. 21, pp. 713–722 (1970).

Shutt, D.A. et al., "The Significance of Equol in Relation to Oestrogenic Responses in Sheep Ingesting Clover With a High Formononetin Content," *Aust. J. Agric. Res.*, vol. 19, pp. 545–553 (1968).

Shutt, D.A. et al., "Steroid and Phyto–Oestrogen Binding to Sheep Uterine Receptors In Vitro," *J. Endocr.*, vol. 52, pp. 299–310 (1972).

Smith, G.R. et al., "Influence of Harvest Date, Cultivar, and Sample Storage Method on Concentration of Isoflavones in Subterranean Clover," *Crop Science*, vol. 26, pp. 1013–1016 (1986).

Trease, G.E. et al., "Pharmacognosy," $12^{th}$ Ed., pp. 242–260 (1983).

Verdeal, Kathey et al., "Naturally–Occurring Estrogens in Plant Foodstuffs—A Review," *J. Food Protect.*, vol. 42, No. 7, pp. 577–583 (1979).

Walter, E.D., "Genistin (an Isoflavone Glucoside) and its Aglucone, Genistein, from Soybeans," *J. Am. Chem. Soc.*, vol. 63, p. 3273 (1941).

Wang, G. et al., "A Simplified HPLC Method for Determination of Phytoestrogens in Soybean and Its Processed Products," *J. Agr. Food Chem.*, vol. 38, No. 1, pp. 185–190 (1990).

White, Edmund et al., "Extracta," *Pharmacopedia*, 2d ed. pp. 166–167 (1909).

Wilcox, G. et al., "Oestrogenic effects of plant foods in post–menopausal women," *British Med. J.*, vol. 301, pp. 905–906 (1990).

Wong, E., "Detection and Estimation of Oestrogenic Constituents in Red Clover," *J. Sci. Food Agric.*, vol. 13, pp. 304–308 (1962).

Wong, E., "The Oestrogenic Activity of Red Clover Isoflavones and Some of Their Degradation Products," *J. Endocrin.*, vol. 24, pp. 341–348 (1962).

"Estrogenic Activity in Plants," Brisbane Seminar (Summary of Talk by Nancy Beckham) (1985).

"Phenolic Constituents," *Soybeans: Chemistry and Technology*, vol. 1, pp. 186–189 (1972).

"Solvent Treatment of Beans and Fractions," *Soybeans: Chemistry and Technology*, p. 149 (1972).

\* cited by examiner

HEALTH SUPPLEMENTS CONTAINING PHYTO-OESTROGENS, ANALOGUES OR METABOLITES THEREOF This is a continuation of application Ser. No. 08/910,837, filed Aug. 13, 1997, now U.S. Pat. No. 6,562,380; which is a continuation of application Ser. No. 08/338,567, filed Jan. 12, 1995, now U.S. Pat. No. 5,830,887; which is a National Stage entry of PCT Application PCT/AU93/00230, filed May 19, 1993; which claims priority of Australian Application PL 2511, filed May 19, 1992; all of which are incorporated herein by reference.

TECHNICAL FIELD

This invention relates to natural products containing phyto-oestrogens, or phyto-oestrogen metabolites, which have various beneficial physiological effects in man, and which have a variety of uses, such as to promote good health and as a dietary additive, for example.

BACKGROUND ART

The particular product in accordance with the invention is an extract of certain plants with the particular purpose of enrichment for phyto-oestrogens, both in their natural state and their closely related derivatives and metabolites.

Plants which are used as foodstuffs or medicinal herbs contain a wide variety of chemicals which are assimilated into the body following ingestion. Some of these chemicals are important nutrients for man and animals (e.g. fats, carbohydrates, proteins, vitamins, minerals) while others have none, or little or no known nutritional value. The phyto-oestrogens hitherto have fallen into this latter category of no known nutritional value.

There are 3 principal classes of phyto-oestrogens, viz. isoflavones, lignans, and coumestans. The isoflavones are thought to have a broad range of biological functions in plants, although these are poorly understood. However, two particular functions are recognised—(a) as phyto-alexin or stressor chemicals which are secreted by the plant in response to attack by parasites such as insects, fungi, viruses, etc and which display activity against these parasites, and (b) chemicals which encourage colonisation of nitrogen-fixing bacteria on the roots of legumes. The biological functions in plants of the lignans and coumestans is not generally understood The different types of phyto-oestrogens are as follows.
Type 1 Phyto-oestrogens—(Isoflavones)

Isoflavones appear to be widely distributed in the plant kingdom and over 700 different isoflavones are described. However, the isoflavones which display oestrogenic activity belong to a small sub-group and are restricted almost exclusively to the Leguminosae family. The known oestrogenic isoflavones are daidzein, formononetin, genistein and biochanin A. In common human foodstuffs such as soya, chickpeas, lentils and beans, the total levels of the oestrogenic isoflavones range between about 40 and 300 mg per 100 g dry weight.

In the raw plant material, isoflavones occur principally as glycosides. Following ingestion by man and animals, the glycoside moiety is hydrolysed free by a combination of gastric acid hydrolysis and fermentation by intestinal bacteria. Some of the isoflavones in the aglucone form are absorbed directly and circulate in the blood, while the remainder are metabolised by intestinal fermentation to a variety of compounds which are also absorbed. The absorbed isoflavones and their metabolites appear to undergo little or no further metabolism in the body, being readily transported in the bloodstream, and ultimately being excreted in the urine.

Type 2 Phyto-oestrogens (Lignans)

Lignans are widely distributed in the plant kingdom. Over one hundred lignans are described and they are reported in common human foodstuffs such as cereals, fruits and vegetables. Oilseeds such as flax (linseed) have the highest known levels at 20–60 mg/100 g dry weight, while cereals and legumes have much lower levels at 0.3–0.6 mg/100 g, and vegetables even lower levels at 0.1–0.2 mg/190 g. The most common lignan described is metairesinol. Dietary lignans also appear to be metabolised fairly efficiently within the gut by bacterial fermentation, yielding metabolites such as enterodiol and enterolactone which are absorbed into the bloodstream and excreted in the urine.

Type 3 Phyto-oestrogens (Coumestans)

Compared to isoflavones and lignans, oestrogenic coumestans appear to have a relatively restricted distribution in plants and generally occur at much lower levels. Alfalfa, ladino clover and some other fodder crops such as barrel medic may have significant levels and have been reported to cause reproductive dysfunction in grazing animals. In the human diet, the important sources of coumestans are sprouts of soya and alfalfa where levels up to 7 mg/100 g dry weight are reported. Whole soyabeans and other common foodstuff legumes contain levels of approx. 0.12 mg/100 g dry weight and most of that is concentrated in the seed hull which commonly is removed in the preparation of human foodstuffs.

Type 4 Phyto-oestrogens (Oestrogens)

These are compounds closely related to animal oestrogens such as oestrone, oestradiol and oestriol. These have been described in plants such as liquorice, apple, French bean, pomegranate and date palm. Little is known of the metabolism and biological significance of these chemicals in humans and animals.

The full range of biological effects in animals of these dietary phyto-oestrogens has received only recent study. A primary effect appears to be associated with their close structural relationship to naturally-occurring oestrogens which allows the phyto-oestrogens to mimic the effects of the endogenous oestrogens. The known biological effects of phyto-oestrogens can be summarised thus:

In vitro
  (a) bind to both cytoplasmic and nuclear membrane (Type II) oestrogen receptors on human tissues;
  (b) strongly compete with oestrogens for oestrogen receptors, but only weakly stimulate those receptors;
  (c) strongly stimulate the production of sex hormone-binding globulin (SHBG) from human cells;
In vivo
  (d) weakly oestrogenic in animals;
  (e) competitively-inhibit the response of tissue to oestrogens.

The three major types of phyto-oestrogens appear to act at the cellular level in a similar manner, that is through interaction with cell surface oestrogen receptors. In the body, naturally-occurring oestrogens circulating in the blood largely exert their activity by interaction with oestrogen receptors on cell surfaces; such interactions then triggering a particular biological function of that particular cell. Phyto-oestrogens are able to bind to those oestrogen receptors because the structure of these compounds so closely resembles the endogenous oestrogens, but unlike the animal oestrogens, phyto-oestrogens only weakly activate the oestrogen receptor.

As a result of phyto-oestrogens and endogenous oestrogens competing for the oestrogen-binding sites on cells, the more weakly oestrogenic phyto-oestrogens can be considered to have an anti-oestrogenic effect. This phenomenon is known as competitive-inhibition, by which is meant that the biological effect of an active substance is impaired by the competitive binding to a target receptor of a similar but less active compound.

Thus a primary biological effect of phyto-oestrogens is held to be competitive inhibition of endogenous oestrogens. However, another more direct effect is the stimulation of synthesis of SHBG in the liver, as occurs with orally administered synthetic steroidal oestrogens. High levels of dietary phyto-oestrogens are thought to be responsible for the higher SHBG levels seen in vegetarians and in cultures maintaining traditional (high legume-containing) diets.

At high levels, dietary phyto-oestrogens can have profound physiological effects. An example of this is sheep and cattle grazing pastures containing a high proportion of subterranean clover or red clover which can contain levels of phyto-oestrogens as high as 5% of the dry weight of the plant. As a result of the competitively-inhibitory effect of the dietary phyto-oestrogens on endogenous oestrogen function in the hypothalamus, male and female sheep and cows can develop androgenic symptoms.

Such high dietary levels of phyto-oestrogens, however, are rare. It is far more common that most animal and human diets contain low to moderate levels of phyto-oestrogens, and there is growing epidemiological evidence that such levels have a beneficial effect on human health.

In most traditional human diets in developing countries, the principal phyto-oestrogens consumed are isoflavones because of the generally high reliance on legumes (also known as pulses) as a source of protein. The general consumption rates (g/day/person) for legumes for different regions currently are approximately: Japan (50–90), India (40–80), South America (30–70), North Africa (40–50), Central/Southern Africa (20–50) and Southern Mediterranean (30–60). Legumes also are a source of lignans and, to a much lesser extent, coumestans, and the additional cereal and vegetables in the diet would also boost the lignan intake. However, the isoflavone intake in these traditional cultures with high legume consumption would typically be much in excess of either lignan or coumestan intake.

The major types of legumes used in traditional diets include soya, chickpeas, lentils, ground nuts, beans (e.g. broad, haricot, kidney, lima, navy), and grams (bengal, horse and green).

In Western, developed countries, the daily intake of dietary phyto-oestrogens generally is negligible to low. In Western Europe, North America and Australasia, legumes were a major source of protein for the majority of the populations up to the end of the 19th century. From that time, legume consumption has declined significantly, being replaced in the diet with protein of animal origin. Average legume consumption in these regions currently is between 5–15 g/day/person with a significant proportion of the population ingesting little to no legumes or other phyto-oestrogen containing foods on a regular basis. Moreover, the types of legumes consumed in these regions (e.g. garden peas, French beans) have a typically lower isoflavone content than legumes such as soya and chick peas.

Based on typical consumption rates and types of foodstuffs consumed, the typical phyto-oestrogen intake (mg/day) for different regions can be calculated approximately as

|  | Isoflavones | Lignans | Coumestans |
|---|---|---|---|
| Japan | 50–300 | 2–5 | 0.5 |
| Australia | 2–25 | 1–5 | 0.2 |

Thus it can be seen that regions which have maintained traditional diets have a higher average daily intake of phyto-oestrogens, particularly isoflavones, compared to western countries. People in communities such as Japan or developing countries with high legume intake excrete substantially higher phyto-oestrogen metabolites in their urine compared to people in Western countries. Within the latter, vegetarians also excrete higher phyto-oestrogen metabolite levels than do those consuming a more typical, omnivorous Western diet.

The presence of relatively large amounts of phyto-oestrogen metabolites in urine serves to highlight their potential biological significance. It has been shown that total urinary excretion of isoflavones and their active metabolites in people consuming moderate amounts of legumes is greatly in excess (up to 10,000×) of steroidal oestrogen levels. So that while the oestrogenicity of isoflavones to oestrogen receptors is only about 1% that of endogenous oestrogens, this weaker effect is off-set by the much higher blood levels of the isoflavones.

It is known that legumes have formed an important part of the human diet over the past 20,000–30,000 years. It therefore follows that human metabolism has evolved over at least this period in the presence of relatively large levels of dietary phyto-oestrogens, particularly isoflavones. Given the known biological effects of phyto-oestrogens, it also follows that endogenous oestrogen metabolism and function has evolved in the face of significant competitive inhibiting effects of phyto-oestrogens. It has been speculated that the presence of significant dietary levels of phyto-oestrogens in recent human evolution has led to a degree of adaption by tissues responsive to reproductive hormones to these dietary components. That is, both the rate of production and/or the function of endogenous oestrogens may be either dependent upon or influenced by the presence of phyto-oestrogens in the body. It follows therefore that a relative deficiency of dietary phyto-oestrogens could be expected to lead to an imbalance of endogenous oestrogen metabolism.

There is increasing interest in the likely contribution of a relative deficiency of dietary phyto-oestrogens to the development of the so-called "Wester diseases", especially cancer of the breast, benign (cystic) breast disease, cancer of the uterus, cancer of the prostate, cancer of the bowel, premenstrual syndrome, menopausal syndrome, and atherosclerosis. All of these diseases are associated to a greater or lesser extent to oestrogen metabolism, and oestrogen function is either known or is suspected to play a role in their aetiology and/or pathogenesis.

Each of these diseases occurs at much higher incidence in Western, developed countries than it does in developing communities. Moreover, it is thought that in Western communities, the incidences of each have risen over the past century. It is also generally held, that of all the environmental factors likely to be contributing to this phenomenon, diet is the principal factor. Of those dietary components with the potential to influence the aetiology of oestrogen-related disease, there is a growing awareness that phyto-oestrogens may have important potential.

The beneficial effects of phyto-oestrogens on human health are thought to derive from at least two principal function, those being (i) competitive-inhibition of the function of endogenous oestrogens, and (ii) the stimulation of production of SHBG. SHBG plays an important role in primates in binding and transporting the reproductive hormones (oestrogens, androgens) in blood so that the availability of reproductive hormones is regulated to a large degree by SHBG levels. Higher SHBG levels are considered beneficial in leading to a reduction in both blood levels of unbound (and unregulated) reproductive hormones and metabolic clearance rates of the hormones. Although isoflavones are potent stimulators of SHBG synthesis, they only weakly bind to SHBG, so that the increased SHBG levels resulting from the dietary isoflavones are largely available for binding to endogenous oestrogens.

In terms of directly identifying the beneficial effects of phyto-oestrogens in amelioration of any or all of the "Western diseases", there are only two examples. In one example, the diets of women, with menopausal syndrome were supplemented with foodstuffs (soya, linseed, red clover) high in phyto-oestrogens, and an alleviation of menopausal symptoms to an extent similar to that obtained with replacement therapy with synthetic oestrogens was achieved; that effect was ascribed to the phyto-oestrogen content of the supplement. In the other example, legumes such as soya and various pulses have been shown to have a hypocholesterolaemic effect in humans; this effect has not been ascribed to phyto-oestrogens, although purified isoflavones do have a hypocholesterolaemic effect in animals with artificially-induced hypercholesterolaemia.

In summary, it could reasonably be deduced that the inclusion of greater levels of foodstuffs high in phyto-oestrogens in the standard diets of men and women in developed countries could be expected to redress a general imbalance of endogenous reproductive hormone metabolism, thereby reducing the predisposition of those communities to the above diseases. While there are various types of phyto-oestrogens which may be suitable to this end, the large discrepancy in isoflavone consumption between communities with Western and traditional diets suggest that foodstuffs with high isoflavone content are of prime interest.

However it is unrealistic to expect that public education programmes would readily convert communities in developed countries from a diet where the protein content is predominantly animal-derived, to one where the protein is predominantly legume-derived. Moreover, the legumes which are commonly consumed in developed countries are relatively poor sources of phyto-oestrogens and the general acceptance in the community of less well-known legumes with higher phyto-oestrogen content would be necessarily a slow process. Also, the highly variable levels of phyto-oestrogens in foodstuffs relating to plant strain type, degree of plant maturity, and climatic and other environmental conditions suggests that the supply of an assured amount of phyto-oestrogens through the use of whole foodstuffs may be difficult.

An alternative strategy is to make available either (i) phyto-oestrogens in a purified form, or (ii) foodstuffs which are enriched for phyto-oestrogens. In this way, the phyto-oestrogen could be added to the diet in a convenient form as a supplement without requiring any substantive change to the diet.

DISCLOSURE OF INVENTION

The present invention concerns a health supplement specifically enriched for isoflavones selected from genistein, daidzein, formononetin and biochanin A, or their natural glycoside form, or their analogues, in sufficient amounts to improve the health of a human.

Preferably the supplement contains an excipient, a diluent, a carrier or the like, or else the supplement is mixed with food or can be consumed directly. It is also preferred that foodstuffs, are readily available, have no known toxic components, and are rich sources of isoflavones; such foodstuffs preferably being red clover or soya. It is also preferred that the ratio of genistein and/or it methylated derivative biochanin A to daidzein and/or its methylated derivative formononetin is between 1:2 to 2:1. Other plant components with oestrogenic activity including lignans, coumestans and flavones may also be present in the extract, but it is held that these are of secondary importance to the predominant isoflavones. The term phyto-oestrogens is used hereafter to indicate a predominance of isoflavones with lesser amounts of lignans, coumestans and flavones.

The invention also concerns a method of improving the health of a human by administering to the human a sufficient amount of phyto-oestrogen. Ideally, the phyto-oestrogen is administered regularly on a daily basis over a sufficient period such as at least a month. The health conditions which may be prevented or ameliorated include cancer of the breast, cancer of the prostate, cancer of the uterus, cancer of the bowel, benign (or cystic) breast disease, pre-menstrual syndrome (also known as pre-menstrual tension), or adverse symptoms associated with menopause in women. The method and supplement in accordance with the invention also improves the health of a human having elevated levels of blood cholesterol. The product also is useful in avoiding or ameliorating cancer in persons. The symptoms produced by these conditions and the general well-being is also improved by the use of these supplements.

The phyto-oestrogen in accordance with the invention may be obtained from a number of different sources. Preferably the phyto-oestrogens are extracted from a clover such as red clover or subterranean clover or from soya which contain high levels of phyto-oestrogens.

However, any source rich in phyto-oestrogens may be used instead, if desired.

Various different isoflavones have been identified from these sources—they are principally genistein, biochanin A, daidzein, formononetin and glycitein. In plants these compounds occur principally in a glycoside form bound to sugars such as glucose, with smaller amounts present as the aglucone forms. The formulae of the isoflavones are:

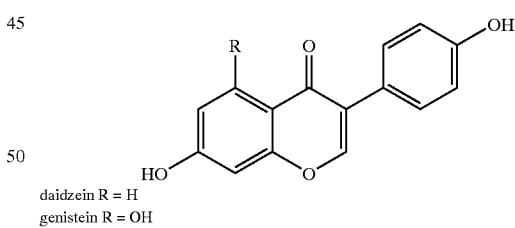

daidzein R = H
genistein R = OH

The structure of biochanin A is the same as for genistein but with a 4'-methoxy group, and similarly formononetin has the same structure as daidzein, but with a 4'-methoxy group.

Following ingestion by humans, the glycosidic isoflavones are hydrolysed to the aglucone form and biochanin A and formononetin are demethylated by bacterial fermentation to genistein and daidzein respectively. A small proportion of these free isoflavones are absorbed directly from the bowel and circulate in the blood. The bulk of the isoflavones, however, remain in the bowel and undergo fermentation to form various metabolites which also are absorbed into the bloodstream. The principal metabolites which have been identified are equol and O-desmethylangolensin.

In vitro and in vivo studies have indicated that genistein, biochanin A, equol, daidzein, formononetin all have oestrogenic activity in descending order. O-desmethylangolensin is only very weakly oestrogenic and glycitein is non-oestrogenic.

In animal and in vitro studies, genistein has been shown to have greater oestrogenic/anti-oestrogenic activity and SHBG-stimulating capacity than the other isoflavones or their metabolites (approximately 10 times that of daidzein and formononetin). However, the full range of biological effects of the different isoflavones have yet to be fully determined, and in particular their relative efficacies in the different biological effects such as oestrogenicity, hypocholesterolaemia, anti-angiogenesis, anti-oxidation, anti-carcinogenesis for example are not yet fully known.

It is thought that because the methyl forms (biochanin A and formononetin) ultimately are largely demethylated to their principals, genistein and daidzein, with improved biological efficacy, then it is unimportant whether the isoflavones are present in the claimed product in the methylated or demethylated forms.

Given that the relative biological importance of the two isoflavone groups (being genistein and daidzein) to human health remains unclear, and that each might indeed have different importance, plus the fact that both isoflavones are present in the diet in approximately equal proportions, then it is prudent that both isoflavones be present in the claimed product in approximately equal proportions.

Any leguminous plants such as detailed here could be used as sources of phyto-oestrogens (principally isoflavones with lesser amounts of lignans and coumestans): Indian liquorice (*Abrus precatorius*); various species of Acacia spp. including, *A. aneura, A. cibaria, A. longifolia,* and *A. oswaldii*; ground nut (*Apio tuberosa*); ground pea (*Arachis hypogea*); milk vetch (*Astragalus edulis*); marama bean (*Bauhinia esculenta*); sword bean (*Cajanus cajan indicus*); jack bean (*Canavalia ensiformis*); sword bean (*Canavalia gladiata*); seaside sword bean (*Canavalia rosea*); various Cassia spp. including *C. floribunda, C. laevigata,* and *C. occidentalis*; carobbean (*Ceratonia siliqua*); chick pea (*Cicer arietinum*); yebnut (*Coideauxia edulis*); various Crotalaria spp. including *C. laburnifolia,* and *C. pallida*; cluster bean (*Cyamopsis psoralioides*); tallow tree (*Detariaum senegalense*); sword bean (*Entada scandens*); balu (*Erythrina edulis*); soyabean (*Clycine max;*) inga (Ingaedulis); Polynesian chestnut (*Inocarpus fagifer*); hyacinth bean (*Lablab purpureus*); grass pea or Indian vetch (*Lathyrus sativus*); cyprus vetch (*Lathyrus ochrus*); lentil (*Lens culinaris*); jumping bean (*Leucaenal eucocephala*); various Lupinus spp. including *L. albus, L. luteus, L. angustifolium, L. mutabilis,* and *L. cosentinii*; ground bean (*Macotylma geocarpa*); horse gram (*Macrotyloma uniflorum*); alfalfa (*Medicago sativa*); velvet bean (*Mucuna pruriens*); yam beans (*Pachyrhyzuz erosus, P. tuberosus*); African locust bean (*Parkia clappertoniana*); *Parkia speciosa*; oil bean tree (*Peniaclethra macrophylla*); various Phaseolus spp. including *P. acutifolius, P. vulgaris, P. luntus, P. coccineus, P. adenathus, P. angulris, P. aureus, P. calcarutus, P. mungo,* and *P. polystachyus*; garden pea (*Pisum sativum*); djenko bean (*Pithecolobium lobatum*); mesquite (various Prosopis spp.); goa bean (*Psophocarpus scandens, P. tetragonolobus*); various Psoralea spp.; *Sesbania bispinosa*; yam bean (*Sphenostylis stenocarpa*); tamarind (*Tamarindus indica*); fenugreek (*Trigonella foenumgraecum*); vetches (various Vivia spp. including *V. sativa, V. atropurpurea, V. ervilia,* and *V. monantha*); broad bean (*Vicia faba*); black gram (*Vigna mungo*); various Vigna spp. including *V. radiata, V. aconitifolia, V. adanatha, V. angularus, V. tribolata, V. umbelata,* and *V. unguiculata,* and, earth pea (*Voandzeia subterranea*).

The ideal sources of phyto-oestrogens for preparation of a supplement in accordance with the invention are preferably those which (i) are readily available, (ii) are relatively inexpensive, (iii) are readily and economically processed so as to yield the extract, (iv) have a high isoflavone content so as to provide high yields, and (v) have no known toxic components requiring selective removal or inactivation.

Certain clovers, such as red clover (*T. pretense*) and subterranean clover (*T. subterranean*) are the preferred sources. On a dry weight basis, these clovers contain the highest amounts of oestrogenic isoflavones of all legumes tested to date with levels of 3–5 g % (*T. subterranean*) and 1–3 g % (*T. pratense*). In comparison, soya flour has a level of 0.15–0.30 g %, lentils (0.08–12 g %), chick peas (0.07–0.13 g %), and garden peas (0.02–0.03 g %). Thus it can be seen that clovers contain approximately at least 10–30 times by weight the isoflavone content of other commonly available, human leguminous foodstuffs meaning that for manufacturing purposes, the yield of isoflavones per unit weight of plant material is many times greater from clover than from other legumes.

Red clover and subterranean clover also are common fodder crops and are readily grown and are widely available. Clovers also are comparatively cheaper ($200/tonne) than crops such as soya and lentils ($500/tonne).

With clovers, the isoflavones are recovered from the leaf rather than from the seed in the case of soya, beans, nuts and grams. This provides a substantially higher yield of isoflavones per unit area of pasture for clovers compared to other legumes because of the greater leaf matter compared to seed matter recovered per plant.

Clovers also have an extended growing season, and faster growth rates compared to those legumes such as soya, lentils or chick peas where the seed is the end-product. Clover can be cropped for its leaf content repeatedly over a single, growing season. An additional benefit of this is that as phyto-alexins, the isoflavone content increases in response to the stress of cropping.

Thus it can be seen that in clovers versus other legumes provide a combination of (a) higher isoflavone content per dry weight of plant, (b) a higher yield of dry matter containing isoflavones per plant, and (c) a higher yield of dry matter per hectare.

An additional feature of clovers is that there are wide varieties of cultivars with widely differing isoflavone levels and types. This allows blending of different cultivars to achieve the desired ratio of the different isoflavones, although it is equally possible to use a single cultivar which provides the desired ratio.

Other legumes such as soyabean flour may be used for enrichment of phyto-oestrogens but the substantially poorer (approx. 10%) yield of isoflavones compared to clovers means that the manufacturing costs are substantially greater and there is substantially greater amounts of waste products which requires disposal or further treatment for re-use as a foodstuff. An alternative, however, to the use of whole soya for this purpose, is to use the hull and hypocotyl (or germ) of the whole soyabean. The hull and hypocotyl represent only a small proportion by weight (8% and 2% respectively) of the intact bean. However, the coumestrol content of soya is concentrated in the hull, and the daidzein content of soya is concentrated in the hypocotyl. The two cotyledons which comprise the bulk of the soyabean (90% by weight) contain the bulk of the genistein content of soya. During standard processing of soyabeans, the hulls being a fibrous component with little or no perceived nutritional value normally are separated and removed by physical means. The hypocotyls become separated following the splitting of the cotyledons, and while these currently generally are not deliberately isolated, they may be separated and isolated by passing the disturbed soyabeans over a sieve of sufficient pore size to selectively remove the small hypocotyl. The hypocotyl contains approx. 1.0–1.5 g % isoflavones (95% daidzein, 5% genistein). The raw hypocotyl and hull material can be ground or milled to produce, for example, a dry powder or flour which then could be either blended or used separately as a dietary supplement in a variety of ways including, for example, as a powder, in a liquid form, in a granulated form, in a tablet or encapsulated form, or added to other prepared foodstuffs. Alternatively, it could be further processed to yield an enriched extract of phyto-oestrogens. Either or both of these materials also could be added to other leguminous material such as clover to provide the invention.

In plants, the oestrogenic isoflavones are restricted principally to the leaf, fruit and root; the stem and petiole contain very little. With soya and other common human legume foodstuff crops, the leaves are rarely regarded as foodstuff; indeed with these crops, the plants normally are allowed to die and dry out before the seed crop is harvested. Nevertheless, the fresh leaves of these crops could be regarded as a source of phyto-oestrogens for the invention although the much lower isoflavone content of the leaves of these crops compared to clovers, plus their generally slow growth compared to clovers, suggests that they would not be a preferred source of large-scale isoflavone enrichment.

To provide a similar amount of isoflavone to that contained in most traditional legume-rich diets (50–100 mg oestrogenic isoflavones/day) would require an average daily consumption of 3–6 g dry weight or 15–30 g wet weight of specially selected cultivars of clover with particularly high isoflavone levels. Clover grasses generally are not eaten by humans, except to a limited extent as sprouts of some of the pleasanter tasting varieties. Isoflavones are intensely astringent and are responsible in large part for the bitter taste of legumes. Thus the types of bean sprouts, clover sprouts and alfalfa sprouts generally available have been selected on the basis of cultivar and of age for pleasant taste, and in so doing inadvertently have been selected for low isoflavone content. Of the sprouts currently available in Western countries for human consumption, between approx. 100–250 g would need to be consumed daily to provide a dosage of 50–100 mg isoflavones. Certainly clovers and other legume sprouts are not generally eaten in such sufficient quantities by humans to obtain the advantages of the present invention The invention also concerns formulations containing the phyto-oestrogens discussed above together with a dietary suitable excipient, diluent, carrier, or with a food. Ideally the formulation is in the form of a pill, tablet, capsule, or similar dosage form.

The formulations may be a variety of kinds, such as nutritional supplements, pharmaceutical preparations, vitamin supplements, food additives or foods supplemented with the specified active phyto-oestrogens of the invention, liquid or solid preparations, including drinks, sterile injectable solutions, tablets, coated tablets, capsules, powders, drops, suspensions, or syrups, ointments, lotions, creams, pastes, gels, or the like. The formulations may be in convenient dosage forms, and may also include other active ingredients, and/or may contain conventional excipients, carriers and diluents. The inclusion of the subject phyto-oestrogens in herbal remedies and treatments is also a preferred part of the invention.

The invention is also directed to the amelioration, prevention, or of various conditions responsive to treatment with the phyto-oestrogen substances of the invention. The preferred amounts to be administered to the human fall within 20–200 mg on a daily basis. More preferably the dosage is from 50–150 mg on a daily basis, and most preferably at a dosage of about 100 mg. If desired greater dosages can be administered for therapeutic reasons. In contrast to prior practices such high dosages were not possible. For example, dosages of up to or greater than 1000 mg may be suitable to treat some conditions. In order to obtain the benefits of the invention, the treatment with the isoflavones should continue for a considerable period, ideally for at least a month, and ideally continuously for the whole period for which the health improvement advantages should accrue.

The product according to the present invention yields a constant and accurately known amount of isoflavones. The product is also ideally a natural product, which has advantages for consumer acceptance, and in accordance with the supposed theory behind the invention may very possibly be one of the main causes for its beneficial effects. Whole legumes have a widely variable isoflavone content due to two main causes: the type of legume and the environmental effect. The type of legume typically has a wide range of isoflavone content. The miligram of isoflavone per hundred gram of whole foodstuff (dry weight) is given in the following table:

| Soya Products | |
| --- | --- |
| Whole Soya | 150–300 |
| Soya Milk | 25–40 (mg per 200 ml) |
| Tofu | 55–95 |
| Lentils | 80–120 |
| Chickpeas | 70–130 |
| Broad beans | 15–20 |
| Garden peas | 15–25 |

Thus common leguminous foodstuffs consumed in Western countries (broad beans, garden peas etc) have relatively low oestrogenic isoflavone content and exceptionally large amounts of these would need to be consumed daily to approximate those isoflavone levels consumed in traditional diets. Most Western cultures do not traditionally eat legumes with high isoflavone contents, and those soya products (milk, tofu etc) which are becoming increasingly popular in Western countries, also have relatively low isoflavone levels compared to whole soya, indicating that relatively large amounts of these would need to be consumed on a regular basis to deliver the required isoflavone levels.

The enviromental effect arises because the isoflavone levels in any species of plant depend greatly on the age of the plant, the climatic conditions where it is grown, the fertiliser and so forth. Therefore constant and consistant dosage is very difficult with ordinary whole foodstuffs. The accurately determined quality and quantity of the active isoflavones in the product, and its easy consumability when compared with the almost impossible task of eating huge amounts of often practically inedible foods, is therefore an import feature of the invention for preventing and helping in overcoming various health problems.

Among the various health problems, the treatment or prevention of high blood cholesterol levels, and the treatment of PMS and menopausal symptoms is especially important. The product of the invention modulates the production and/or function of endogenous sex hormones in humans to modify or produce health improving effects, including the following: (i) lowered levels of various blood lipoproteins including, for instance, low-density and very-low-density cholesterol leading to reduced risk of development of atherosclerosis; (ii) reduced risk of development of cancer of the prostate; (iii) reduced risk of cancer of the breast; (iv) reduced risk of development of cancer of the uterus; (v) reduced risk of development of cancer of the large bowel; (vi) reduced risk of development of the syndrome in women commonly referred to pre-menstrual syndrome (PMS), which includes pre-menstrual tension (PMT); (vii) reduced risk of development of many untoward symptoms (including dry vagina, peripheral flushing, depression etc) commonly associated in women with menopause; and for treating benign breast disease in women (benign or cystic breast disease associated with non-malignant swelling and tenderness of breast tissue). The invention therefore is directed to a method for the prophylaxis or treatment of a human, to combat conditions associated with phyto-oestrogen deficiency, which comprises administering to the human an effective amount of phyto-oestrogen principally isoflavone but which might also include relatively smaller amounts of lignans and coumestans, ideally in a concentrated form, wherein the isoflavones include genistein, and/or biochanin A, and/or daidzein, and/or formononetin.

Cancer of the breast generally is considered to be associated with oestrogenic dysfunction. Breast cancer cells may display more oestrogen receptors than normal breast cells and stimulation of these receptors by endogenous oestrogens is thought to be a prime source of stimulation of their malignant growth. Currently synthetic anti-oestrogens are being used to prevent or treat the growth of malignant breast cells. Isoflavones are potent anti-oestrogens that could be expected to help prevent or to successfully treat breast cancer. It has been reported that the risk of breast cancer in western societies is indirectly proportional to the level of phyto-oestrogens in the diet and to the amounts of phyto-oestrogen metabolites excreted in the urine.

Cancer of the prostate generally is considered to be associated with sex hormone dysfunction and the growth of prostatic cancer cells is influenced by oestrogens and androgens. The incidence of prostatic cancer is low in communities with high legume intake and, conversely, is high in Western socieites. Phyto-oestrogens are though to protect from development of prostatic cancer. One mechanism may be the effect of phyto-oestrogens on lowering the proportion of unbound:bound reproductive hormones in the blood. However, there is other evidence to suggest that phyti-oestrogens, particularly isoflavones, can have a direct influence on certain cellular enzymes within prostatic cells.

Pre-menstrual syndrome has uncertain aetiology and pathogenesis, although most certainly is associated with reproductive hormone dysfunction. It also is a syndrome which has reportedly lower incidence in communities maintaining traditional high-legume diets. It is proposed that phyto-oestrogens will alleviate this condition by restoring balance to oestrogen metabolism.

Menopausal syndrome is associated with changes in the oestrogen profile in the body with advancing age. Adverse clinical symptoms may be treated with oestrogen replacement therapy. There is evidence that foodstuffs high in phyto-oestrogens are a suitable alternative to synthetic hormones in this respect, producing alleviation of adverse clinical symptoms. Again, it is proposed that phyto-oestrogens will function by restoring balance to oestrogen metabolism.

Benign (or cystic) breast disease has unknown aetiology. However, its association in women with certain stages of the menstrual cycle is strongly suggestive of oestrogen dysfunction. There currently is no successful treatment of this condition. Phyto-oestrogens are proposed to successfully treat this condition by restoring balance to oestrogen metabolism. Atherosclerosis is associated with cholesterol metabolism which in turn is associated closely with oestrogen metabolism. The generally higher incidence of atherosclerosis in young men versus young women, the rising incidence in women following menopause, and the lower incidence in post-menopausal women receiving oestrogen replacement therapy, all point to the moderating influence of oestrogens on cholesterol metabolism. A prime effect of oestrogens on cholesterol metabolism is stimulation of the liver to process cholesterol, particularly the highly atherogenic low-density lipoproteins and very low-density lipoproteins, into bile salts. It is proposed that phyto-oestrogens have an important hypocholesterolaemic effect in humans. There may be a variety of mechanisms involved, but one may be the stimulation by phyto-oestrogens of cholesterol catabolism by the liver.

MODES FOR CARRYING OUT THE INVENTION

The invention is now described with reference to various examples.

EXAMPLE 1

Preparation of Red Clover Product

Tablets were prepared using red clover in accordance with the following procedure. The raw plant material is harvested and dried; such drying being either sun-drying or from applied heat.

The dried product is then preferably chaffed, before the following extraction step, although this can be omitted if desired.

The dried material is extracted in an aqueous: organic solvent mix. The aqueous phase is required to extract the water-soluble glycoside form of isoflavones, while the organic solvent is required to solubilise the water-insoluble aglycone form. The organic solvent can be either alcohol, chloroform, acetone or ethyl acetate. The ratio of solvent in the water can be between 0.1% and 99.9%. The preferred method is to use 60% alcohol in water.

The isoflavones are extracted by exposing the plant material to the water:solvent mix. The exposure time in general terms is indirectly proportional to the temperature of the mixture. The temperature of the mix can range between ambient temperature and boiling temperature. The exposure time can be between 1 hour and 4 weeks or even longer. It has been determined that the adequate times for maximal recovery of isoflavones are 2 weeks at 50° C. and 24 hours at 90° C. The supernatant is separated from the undissolved plant material and the organic solvent removed by distillation. The aqueous supernatant then is concentrated, typically by distillation.

Additional processing steps can be used, if desired, to convert the extracted natural product to capsule, tablet, or other convenient form for ingestion, using normal techniques for doing this. Otherwise the product can be packaged as a convenient food additive.

EXAMPLE 2

Preparation of Soya hypocotyl Product

Soyabeans were heated in dry air so that the hull became brittle. The beans then were processed through a tumble mill which removed the hull and split the bean the two cotyledons and the small-sized hypocotyl which separated from each other. The light-weight hulls then were removed by an air stream. The small-sized hypocotyls were separated from the larger cotyledons by sieving through a steel wire mesh with apertures of 1 mm×1 mm. This yielded approximately 87% purity of hypocotyls with 13% contamination by small cotyledon chips.

Normal soybean processing steps isolate the hulls and then these are discarded or processed separately for use in human and animal foodstuffs. The hypocotyls normally are not separated and are processed along with the cotyledons. However, a small number of soybean processors are separating hypocotyls by the above methods in order to reduce the astringent taste of soyflour for human consumption, and currently these hypocotyls are either discarded or processed to flour for use in animal feed.

EXAMPLE 3

Effect of Administering Red Clover Extract to Humans

Seven normal individuals were studied for the comparative effects of red clover extract and whole legumes on blood cholesterol levels. All the individuals were consuming a standard Western diet with minimal levels of legumes.

Three men consumed between 100–150 g haricot or navy beans daily for 3 weeks as a supplement to their normal diet. This yielded an approximate daily isoflavone dosage or between 60–100 mg.

Four other individuals (3 men, 1 woman) consumed 5 g of red clover extract containing 100 mg isoflavones daily for 3 weeks.

Total serum cholesterol levels were determined immediately before and immediately following the challenge.

|  | Pre-treatment | Post-treatment | % change |
|---|---|---|---|
| Beans only | | | |
| Patient 1 | 5.77 | 5.46 | −5.4 |
| Patient 2 | 6.24 | 6.12 | −1.9 |
| Patient 3 | 7.45 | 8.51 | +14.3 |
| Red clover extract | | | |
| Patient 5 | 6.53 | 5.90 | −9.6 |
| Patient 6 | 7.43 | 6.63 | −10.8 |
| Patient 7 | 6.33 | 5.50 | −13.1 |
| Patient 8 | 6.98 | 7.28 | +4.3 |

The red clover extract had a significantly (P<0.05) greater hypocholesterolaemic effect than did the whole beans.

Neither of the treatments produced any untoward side effects, although the whole bean eaters reported greater difficulty with compliance of treatment than did those taking the red clover extract.

EXAMPLE 4

Effect of Administering Soy hypocotyls to Humans

Fifteen volunteers (8 women, 7 men) were given 5 g of soy hypocotyl containing (45 mg daidzein and 5 mg genistein) daily for 2 months. The hypocotyl was consumed as a powder added to the diet.

The effects on cholesterol levels are shown in the following table. The individuals are grouped according to their pre-treatment cholesterol levels (high, medium, low).

|  |  | Range (mean) unmol/L | |
|---|---|---|---|
|  | n | Pre-treatment | Post-treatment |
| Group 1 | 6 | 6.3–8.4 (7.1) | 5.4–6.5 (6.1) |
| Group 2 | 6 | 5.0–6.2 (5.5) | 4.7–5.9 (5.1) |
| Group 3 | 3 | 3.3–4.7 (4.2) | 3.4–4.6 (4.1) |

The results show a significant fall in total cholesterol levels in those individuals with cholesterol levels considered to be at the upper end of the normal range.

In addition, 1 woman reported substantial amelioration of her benign breast disease problem associated with mid-cycle swelling and tenderness, and another woman reported regularisation of her menstrual cycle and reduced menstrual bleeding. Both of these effects were regarded as beneficial.

No other side-effects were reported as a result of the treatment.

What is claimed is:

1. A health supplement comprising a health supplementary amount of a naturally occurring phyto-oestrogen selected from any two or more of genistein, daidzein and/or their glycosides.

2. The supplement according to claim 1 which also comprises at least one dietary suitable excipient, diluent, carrier or food.

3. The supplement according to claim 1 wherein said phyto-oestrogen is extracted from soya.

4. The supplement according to claim 3 wherein said phyto-oestrogen is extracted from soya hypocotyls.

5. The supplement according to claim 1 wherein said phyto-oestrogen comprises genistein:daidzein in a ratio of from about 1:2 to 2:1.

6. The supplement according to claim 1 in unit dosage form, wherein said phyto-oestrogen is present in an amount of from about 20 mg to 200 mg per dosage unit.

7. The supplement according to claim 6, where the amount is 50 to 150 mg.

8. The supplement according to claim to 1, which is in the form of a tablet or capsule.

9. The supplement according to claim 7, wherein the amount is 60 mg to 100 mg per dosage unit.

10. The supplement according to claim 1 in unit dosage form, wherein said phyto-oestrogen is present in an amount of about 1,000 mg per dosage unit.

11. The supplement according to claim 1, further comprising at least one of a coumestan, lignan, or a flavone.

12. The supplement according to claim 1, further comprising glycitein.

13. The supplement according to claim 1 wherein said phyto-oestrogen comprises genistein:diadzein present in a ratio of about 1:19.

14. The supplement according to claim 1 wherein said phyto-oestrogen comprises genistein:diadzein present in a ratio of about 1:9.

15. A supplement according to claim 3, wherein the said phyto-oestrogen comprises genistein:daidzein in a ratio of 1:2 to 2:1.

16. The supplement according to claim 15, which is in the form of a tablet or capsule.

17. The supplement according to claim 16 in unit dosage form, wherein said phyto-oestrogen is present in an amount of from about 20 mg to 200 mg per dosage unit.

18. The supplement according to claim 17, wherein the amount is 50 mg to 150 mg per dosage unit.

19. The supplement according to claim 18, wherein the amount is 60 mg to 100 mg per dosage unit.

20. The supplement according to claim 3, further comprising glycitein.

21. The supplement according to claim 3 wherein said phyto-oestrogen comprises genistein:diadzein present in a ratio of about 1:19.

22. The supplement according to claim 3 wherein said phyto-oestrogen comprises genistein:diadzein present in a ratio of about 1:9.

* * * * *

UNITED STATES PATENT AND TRADEMARK OFFICE
CERTIFICATE OF CORRECTION

PATENT NO. : 6,642,212 B1  
DATED : November 4, 2003  
INVENTOR(S) : Graham Edmund Kelly It is certified that error appears in the above-identified patent and that said Letters Patent is hereby corrected as shown below:

<u>Title page,</u>  
Item [57], ABSTRACT,  
Line 2, "Diadzein," should read -- Daidzein, --; and  
Lines 2-3, "Formononectin" should read -- Formononetin --.

<u>Column 14,</u>  
Line 39, "claim to 1," should read -- claim 1, --.  
Lines 51 and 54, "genistein:diadzein" should read -- genistein:daidzein --.

<u>Column 15,</u>  
Line 4, "genistein:diadzein" should read -- genistein:daidzein --.

<u>Column 16,</u>  
Line 2, "genistein:diadzein" should read -- genistein:daidzein --.

Signed and Sealed this

Sixth Day of July, 2004

JON W. DUDAS  
*Acting Director of the United States Patent and Trademark Office*